United States Patent [19]

Cullinan

[11] Patent Number: 4,596,676

[45] Date of Patent: Jun. 24, 1986

[54] BIFUNCTIONAL ESTER DERIVATIVES OF 4-DESACETYL INDOLE-DIHYDROINDOLE ALKALOIDS

[75] Inventor: George J. Cullinan, Trafalger, Ind.

[73] Assignee: Lilly Industries Limited, London, England

[21] Appl. No.: 593,442

[22] Filed: Mar. 26, 1984

[30] Foreign Application Priority Data

Mar. 30, 1983 [GB] United Kingdom ............... 8308856

[51] Int. Cl.[4] .................. C07D 519/04; C07K 15/00; A61K 31/475
[52] U.S. Cl. ............... 260/244.4; 530/391; 530/816
[58] Field of Search ............ 260/244.4; 424/262

[56] References Cited

U.S. PATENT DOCUMENTS

| | | | |
|---|---|---|---|
| 3,387,001 | 6/1968 | Hargrove | 260/244.4 |
| 3,392,173 | 7/1968 | Hargrove | 260/244.4 |
| 4,029,663 | 6/1977 | Gutowski et al. | 260/244.4 |
| 4,046,722 | 9/1977 | Rowland | 260/6 |
| 4,075,214 | 2/1978 | Katner et al. | 260/244.4 |
| 4,087,429 | 5/1978 | Katner et al. | 260/244.4 |
| 4,122,082 | 10/1978 | Wright et al. | 260/244.4 |
| 4,166,810 | 9/1979 | Cullinan et al. | 260/244.4 |
| 4,195,022 | 3/1980 | Thompson | 260/244.4 |
| 4,199,504 | 4/1980 | Conrad et al. | 260/244.4 |
| 4,203,898 | 5/1980 | Cullinan et al. | 260/244.4 |
| 4,522,750 | 6/1985 | Ades et al. | 260/112 R |

FOREIGN PATENT DOCUMENTS

| | | |
|---|---|---|
| 124502 | 4/1980 | European Pat. Off. . |
| 41935 | 12/1981 | European Pat. Off. . |
| 2090837 | 1/1982 | United Kingdom . |

OTHER PUBLICATIONS

Cullinan et al., Chemical Abstracts, vol. 102, 160,418v (1985), abstract of Eur. Pat. Appl. 121,388, 10/10/84.
Trouet et al., Chemical Abstracts, vol. 102, 160,419w (1985), abstract of Euro. Pat. Appl. EP 124,502 11/07/84.
Cullinan, Chemical Abstracts, vol. 102, 204156q (1985), abstract of Brit. UK Pat. Appl. GB 2,137,202, 10/03/84.
Barnett et al., J. Med. Chem., 21, 88–96 (1978).
Conrad et al., J. Med. Chem., 22, 391–400 (1979).
Root et al., FACSS Abs. pp. 124–125 (Oct. 6–10, 1975) (abstract).
Langone et al., Anal. Biochem., 95, 214 (1979).
Teale et al., Brit. J. Clin. Pharm., 4, 169–72 (1977).
Johnson et al., Brit. J. Cancer, 44, 472–75 (1981).
Johnson et al., Cancer Research, 26, 2431–36 (1966).
Hargrove, Lloydia, 27, 340–345 (1964).

Primary Examiner—Donald G. Daus
Assistant Examiner—Diana G. Rivers
Attorney, Agent, or Firm—James L. Rowe; Arthur R. Whale

[57] ABSTRACT

Bifunctional ester derivatives at C-4 carbon of dimeric indole-dihydroindole alkaloids; e.g., VLB 4-hemisuccinate.

21 Claims, No Drawings

BIFUNCTIONAL ESTER DERIVATIVES OF 4-DESACETYL INDOLE-DIHYDROINDOLE ALKALOIDS

BACKGROUND OF THE INVENTION

The alkaloids obtainable from *Vinca rosea* represent one of the most productive areas of chemistry for drugs which adversely affect the growth of experimental malignancies in mammals. Initially, only some of the alkaloids, obtainable from the leaves of the plant by extraction and purifiable by chromatography, were found to be active. These active antineoplastic alkaloids obtained directly from the leaves of the vinca plant incude VLB (Vinblastine, vincaleucoblastine), vincristine (leurocristine), leurosine (vinleurosine), leurosidine (vinrosidine), leuroformine (formylleurosine) and deoxy VLB "A" and "B" (4'-deoxy VLB and 4'-deoxyleurosidine).

Chemical modification of the Vinca alkaloids started slowly for several reasons. In the first place, the molecular structures involved are extremely complex, and chemists were slow to find reactions which modified one specific functional group of the molecule without affecting other groups. Secondly, dimeric alkaloids lacking desirable chemotherapeutic properties had been recovered or produced from *Vinca rosea* extracts, and a determination of their structures had led to the conclusion that these inactive compounds were closely related structurally to, and even isomeric with, one or more of the active alkaloids. Thus, it appeared that small chemical changes in the known anticancer alkaloids could have a profound effect on antineoplastic activity.

Because of these restrictions, modification of the indole-dihydroindole alkaloids obtained from *Vinca rosea* has centered around only three areas of the molecule: C-3, C-4' and C-4. Considering C-3 modification first, one of the more recent, and more successful, modifications of the basic indole-dihydroindole structure has been the preparation of C-3 carboxamide and carboxhydrazide derivatives, most of which turned out to be active anti-tumor agents. [See U.S. Pat. No. 4,166,810, and Conrad et al. *J. Med. Chem.*, 22, 391 (1979)]. 4-Desacetyl VLB 3-carboxamide (vindesine) is currently being marketed in several European countries as an oncolytic agent. It is said to be effective in treating some vincristine-resistant leukemias in addition to many common neoplasms including germ-cell tumors. Reaction of the 3-hydroxy and 3-ester functions with an isocyanate has produced the corresponding oxazolidinedione derivatives, one of which, the N-chloroethyl derivative—vinzolidine—is currently undergoing a clinical trial. These oxazolidinedione derivatives are disclosed in Miller and Gutowski, RE 30,560, reissued Mar. 31, 1981.

A second area of the molecule which has been modified is the C-4' functionality. A majority of these modifications have been based on the 3',4'-anhydro derivative, makeable both by coupling vindoline and catharanthine via a modified Polonovski reaction—Potier et al. *J.C.S. Chem. Comm.*, 670, (1975)—and by dehydrating VLB or leurosidine—Gutowski and Miller, U.S. Pat. No. 4,029,663. The dehydration reaction produces two exo-double bond isomers in addition to the $\Delta^{3',4'}$-anhydro derivative. Functionalization of any one of these double bonds to form epoxides, diols, etc. has constituted the chief chemical modifications undertaken at C-4'.

The third region of the indole-dihydroindole which has been modified successfully is C-4. In the first place, hydrolysis of the acetoxy group, present in all the above vinca alkaloids, yields active antineoplastic 4-desacetyl derivatives. (Vindesine, a C-3 carboxamide, is a 4-desacetyl derivative.) Secondly, Hargrove, U.S. Pat. Nos. 3,387,001 and 3,392,173 prepared novel 4-acyl derivatives of 4-desacetyl VLB, 4-desacetyl vincristine, etc. Among these new derivatives was 4-chloroacetyl VLB, which compound could be reacted with amines, for example, dimethylamine, to yield a potent anticancer drug, vinglycinate, N,N-di-methyl 4-glycinyl VLB. In a different modification, Wright and Neuss, U.S. Pat. No. 4,122,082, oxidized the 4-hydroxyl of 4-desacetyl VLB to a 4-keto compound, and Thompson, U.S. Pat. No. 4,195,022, reduced this ketone to the 4-epihydroxy ($4\alpha$-hydroxy) derivative, also a compound with anticancer activity.

Indole-dihydroindole bridged dimers; i.e., the same or different alkaloid moieties bridged thru the 3-carboxyl via a bis-amide are described in Conrad and Gerzon, U.S. Pat. No. 4,199,504. Otherwise, indole-dihydroindole vinca alkaloid dimers have not been bridged through other positions in the molecule to form vinca tetramers.

VLB and vincristine have been conjugated with proteins to form antigens useful in radioimmune assays. 4-Desacetyl VLB 3-carboxazide (desacetyl vinblastinoic azide) and the corresponding vincristine compound have been the derivatives employed; see Conrad et al., *J. Med. Chem.*, 22, 391 (1979), European Pat. No. 41,935, Abstract 182, FACSS, Oct. 6, 1975, and U.S. Pat. No. 4,203,898 for illustrations of this reaction.

DESCRIPTION OF THE INVENTION

This invention provides compounds of the formula

$$R-O-CO-X-CO-Z \qquad \text{I}$$

wherein R is a dimeric indole-dihydroindole radical (II) derived from a 4-acetoxy or 4-hydroxy antineoplastic dimeric indole-dihydroindole alkaloid,

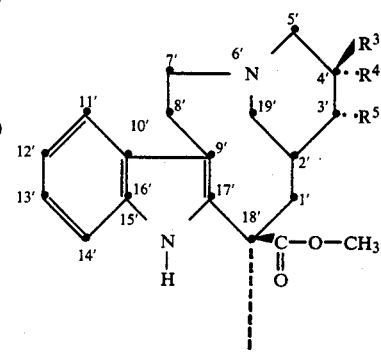

-continued

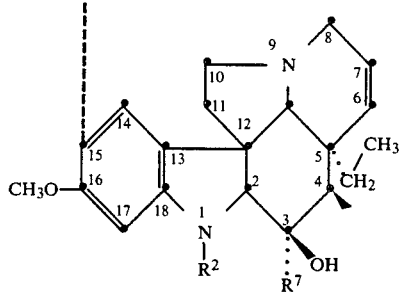

wherein $R^2$ is H, $CH_3$ or CHO; when $R^4$ and $R^5$ are taken singly, $R^5$ is H, and one of $R^3$ and $R^4$ is ethyl and the other is H or OH; when $R^4$ and $R^5$ are taken together with the carbons to which they are attached, they form an oxirane ring in which case $R^3$ is ethyl; and $R^7$ is $COOC_{1-3}$ alkyl or $CO-R^9$, wherein $R^9$ is $NH_2$, $NH-C_{1-3}$ alkyl, $NH-CH_2CH_2Cl$, 1-pyrrolidyl, 1-piperidinyl, or $NH-CH_2CH_2YCH_3$ wherein Y is S or O, and wherein Z is OH, $OC_{1-3}$ alkyl, $OR^1$ wherein $R^1$ is R (same or different), Cl, Br, $N_3$, $NH_2$, $NHNH_2$, imidazolyl, succinimidoxy
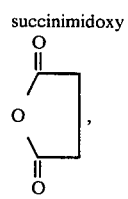

phthalimidoxy
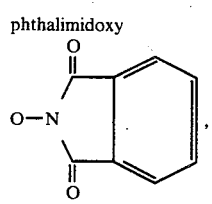

benzotriazolyloxy
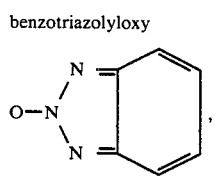

methanesulfonyloxy, tosyloxy, benzenesulfonyloxy or the like acylating groups ($Z^1$) or $CCl_3CH_2O$, $CBr_3CH_2O$, $CH_2ICH_2O$, benzyloxy, methylbenzyloxy, t-butyloxy, allyloxy, methoxybenzyloxy, nitrobenzyloxy, phenacyloxy, nitrophenacyloxy, methoxyphenacyloxy, methylphenacyloxy, diphenylmethyloxy, trityloxy, (triphenylmethyloxy), trimethylsilyloxy or the like carboxy protecting groups ($Z^2$); X is $C_{1-4}$ straight chain alkylene, $C_{2-8}$ branched chain alkylene, $C_{2-4}$ alkenylene, $C_{3-4}$ alkynylene, $C_{3-6}$ cycloalkylene, phenylene, hydroxy-substituted $C_{1-4}$ alkylene or a direct bond; and acid addition salts thereof.

A second aspect of this invention involves compounds of the structure $$R^{11}-O-CO-X-CO-Z^3 \qquad III$$

in which $R^{11}$ is a dimeric indole-dihydroindole C-3 carboxylic acid or derivative thereof represented by IV below:

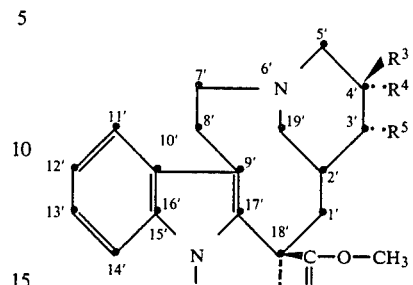

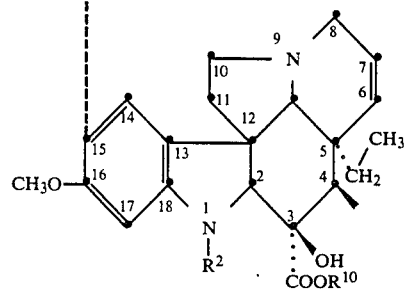

wherein $R^2$, $R^3$, $R^4$ and $R^5$ have their previously assigned meaning and $R^{10}$ is H or $Z^2$, a carboxy protecting group; in which $Z^2$ and X have their previously assigned meanings and $Z^3$ is $OR^1$, OH, $NHNH_2$, $NH_2OH$, $OC_{1-3}$ alkyl, or $Z^1$, an acylating group as defined above. Also included are acid addition salts, and also cationic salts of the C-3 carboxylic acid group, when R is $R^{11}$ and $R^{10}$ is H, such as the sodium, potassium, tetramethyl ammonium and the like.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxyalkanoic and hydroxyalkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycollate, malate, naphthalene-1-sulfonate, naphthalene-2-sulfonate, mesylate and the like salts.

The compounds of this invention in which Z in formula I is $OR^1$, OH or $O-C_{1-3}$ alkyl have utility as antitumor compounds in transplanted tumors in mice, and also possess antimitotic properties.

When Z in formula I or $Z^3$ in formula III is a carboxy activating (acylating) group, it can be any of the well known groups employed in the chemical art and in particular those used in peptide chemistry as carboxy activating groups. Such groups are discussed, for example, in *Peptide Synthesis*, M. Bodanszky, Y. S. Klausner and M. A. Ondetti, Second Edition (John Wiley & Sons, New York, N.Y., 1976) notably pages 85 to 136.

When Z or $Z^3$ are carboxy protecting groups ($Z^2$), they can be any of the other well-known groups employed for this purpose in addition to those set forth above. The term "carboxy protecting group" refers to the commonly used carboxylic acid protecting groups employed to block or protect the carboxylic acid functionality while reactions involving other functional sites of a compound are taking place. Such carboxy protecting groups are noted for their ease of cleavage by hydrolytic or by hydrogenolytic methods to yield again the original carboxylic acid.

Groups illustrative of X in the above formulas include methylene, ethylene, propylene, butylene, vinyl, propenylene, butenylene, butynylene, ethynylene, hydroxyethylene, 1,2-dihydroxyethylene, 1,2-dimethylethylene, 1,2,3,4-tetrahydroxybutylene, 3,4-dimethylbutylene, 1,4-cyclohexylene, 1,4-phenylene, 1,2-phenylene and the like.

The synthesis of the compounds of this invention is carried out in stepwise fashion. First, a 4-desacetyl indole-dihydroindole of the formula ROH, prepared by following the procedure of Hargrove, U.S. Pat. No. 3,392,173, is acylated with a carboxylic acid anhydride of formula V

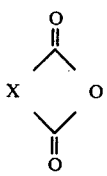

V wherein X has its previous meaning, to yield a compound of formula I wherein Z is OH and R and X have their previous meaning. Compounds wherein Z is $O-C_{1-3}$ alkyl are prepared from the half-acid, R—CO—X—COOH, via one of the usual esterification procedures using a $C_{1-3}$ alkanol. Methanol is the preferred alkanol since the other ester groups present in starting materials of the formula ROH are methyl esters and transesterification problems are thus largely avoided.

When an indole-dihydroindole of formula IV is to be reacted with succinic hydride or the like to prepare a compound according to formula III, the C-3 ester group as well as the C-4 ester group must be hydrolyzed initially to yield, for example from VLB, a 4-desacetyl vinblastinoic acid—see U.S. Pat. No. 4,012,390. Next, the C-3 carboxyl group must be protected with a carboxy protecting group $Z^2$ as defined above. This C-3 carboxy protected derivative having a free hydroxyl at C-4 is then reacted as above with an anhydride (V) to yield the intermediate $R^{11}$—O—CO—X—CO—$Z^3$ in which $R^{10}$ is $Z^2$ in $R^{11}$ and $Z^3$ is OH. This intermediate can then be manipulated chemically to yield compounds according to III in which $Z^3$ is an acylating moiety provided reaction conditions are neutral or basic, thus avoiding removal of the C-3 carboxy protecting group. After the desired terminal group, $Z^3$, is in place, the carboxy protecting group $Z^2$ at C-3 can be removed to yield compounds according to III above in which $R^{10}$ is H.

Alternatively, compounds of the formula

R—O—CO—X—CO—$OC_{1-3}$ alkyl or $R^{11}$—O—CO—X—C—$OC_{1-3}$ alkyl can be prepared directly by using a half ester, half acid chloride as the acylating agent; i.e., Cl—CO—X—CO—O—$C_{1-3}$ alkyl. Other acylating groups can be used in place of Cl, and the acylating moiety can be represented generally by the formula $Z^1$—CO—X—CO—$OC_{1-3}$ alkyl wherein X has its previous meaning and $Z^1$ is Cl, Br, $N_3$, succinimidoxy, phthalimidoxy, methanesulfonyloxy, tosyloxy, phenylsulfonyloxy, benzotriazolyloxy, or other acylating moiety as before. Alternatively, an acylating agent of the formula $Z^1$—CO—X—CO—$Z^2$ where $Z^2$ is a carboxy protecting group, can be used to yield a compound of the formula R—O—CO—X—CO—O—$Z^2$ or $R^{11}$—O—CO—X—CO—O—$Z^2$ although it should be recognized in this later case that another carboxy protecting group may be present on the C-3 carboxyl.

Compounds according to I in which Z is $NH_2$ or $NHNH_2$ are prepared by forming an "activated" vinca dimer (R group) 4-hemi acid of the formula

R—O—CO—X—CO—$Z^1$ where $Z^1$ is preferably Cl. A mixed anhydride is formed from the half-acid by treatment successively with N-methylmorpholine and an alkyl chloroformate. Reaction of the mixed anhydride with alcoholic ammonia or hydrazine yields the desired half-amide. If $R^{11}$—O—CO—X—CO—$Z^3$ is to be prepared where $Z^3$ is $NH_2$ or $NHNH_2$, standard basic reactions can be employed provided $R^{10}$ in $R^{11}$ is a carboxy-protecting group $Z^2$.

Compounds in which Z or $Z^3$ are $OR^1$ in which $R^1$ is also an indole-dihydroindole radical represented by II are prepared by forming an acylating moiety of the formulas R—O—CO—X—CO—$Z^1$ or $R^{11}$—O—CO—X—CO—$Z^1$ (where $R^{10}$ in $R^{11}$ is $Z^2$) and reacting it with the same or different 4-desacetyl indole-dihydroindole alkaloid, $R^1$OH. The carboxy protecting group in $R^{11}$ can then be removed by acid treatment to yield compounds in which $R^{10}$ in $R^{11}$ is H.

Alternative procedures for preparing several of the compounds of formula I involve the use of a coupling agent such as DDC—dicyclohexylcarbodiimide—, EEDQ-N-ethoxycarbonyl-2-ethoxy-1,2-dihydroquinoline—etc. under anhydrous reaction conditions with a half-acid HO—CO—X—CO—$Z^2$, wherein $Z^2$ is a carboxy-protecting group. For example, an initial 4-succinoxy derivative can be prepared from ROH and HO—CO—X—CO—$Z^2$ in the presence of DCC to yield a compound of the formula

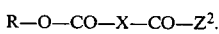
R—O—CO—X—CO—$Z^2$.

The carboxy protecting group can then be removed and the resulting free acid reacted with hydroxyphthalimide, hydroxybenzotriazole, hydroxysuccinimide or the like to yield reactive acylating intermediates of the formula

R—O—CO—X—CO—$Z^4$ wherein $Z^4$ is succinimidoxy, benzotriazolyloxy or phthalimidooxy. These intermediates are then reacted with a second same or different indole-dihydroindole, $R^1OH$ to form a bridged vinca tetramer or can be reacted with protein to form conjugates useful, for example, in a radioimmune assay or can be conjugated with polyclonal or monoclonal antibodies to yield anticancer drugs. In addition, the "activated" derivatives can be reacted with a lower alcohol to yield half esters of the formula

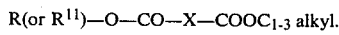
R(or $R^{11}$)—O—CO—X—COO$C_{1-3}$ alkyl.

Generally, the compounds of this invention of the structure R(or $R^{11}$)—O—CO—X—CO—$Z^1$ where $Z^1$ is Cl, Br, tosyloxy, benzenesulfonyloxy, methanesulfonyloxy, succinimidoxy, $N_3$ or other acylating moiety and $R^{10}$ in $R^{11}$ is H after hydrolysis of the carboxy protecting group $Z^2$, are useful not only in preparing those compounds of this invention wherein R or $R^{11}$ and Z or $Z^3$ both contain indole-dihydroindole alkaloid radicals, but as stated above, are also useful for coupling to monoclonal antibodies and to protein so as to provide suitable immunogens for radioimmune assay purposes, as set forth in the copending application of Cullinan, Rowland and Simmonds, Ser. No. 593,443 filed Mar. 26, 1984.

Starting 4-desacetyl indole-dihydroindole alkaloids (ROH, $R^1OH$ or $R^{11}OH$ in which $R^{10}$ is H) useful in forming the compounds of this invention, can be represented by the following 2-dimensional structure III
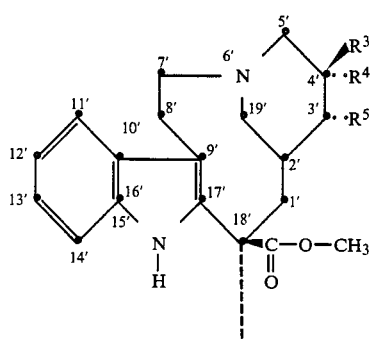

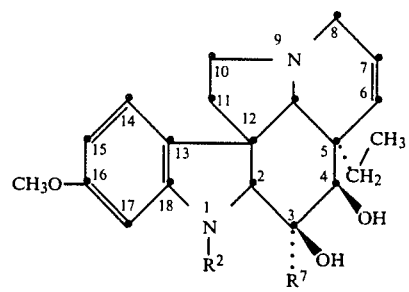

wherein $R^2$ is H, $CH_3$ or CHO; when $R^4$ and $R^5$ are taken singly, $R^5$ is H and one of $R^3$ and $R^4$ is ethyl and the other is H or OH; when $R^4$ and $R^5$ are taken together with the carbons to which they are attached, they form an oxirane ring, in which case $R^3$ is ethyl; and $R^7$ is COO$C_{1-3}$ alkyl, or CO$R^9$ wherein $R^9$ is $NH_2$, NH—$C_{1-3}$ alkyl, NH—$CH_2CH_2Cl$, 1-pyrrolidyl, 1-piperidinyl or NH—$CH_2CH_2YCH_3$ wherein Y is S or O. Ccompounds represented by III above useful in forming those derivatives in which $R^{11}$ is the starting material are also represented by III except that $R^7$ is COOH or COO$Z^2$.

In the above formula, where $R^7$ is CO—$OCH_3$, $R^2$ is methyl, $R^3$ is hydroxyl, $R^4$ is ethyl and $R^5$ is H, 4-desacetyl VLB (4-desacetyl vinblastine) is represented; where $R^7$ is CO—$OCH_3$, $R^2$ is formyl, $R^3$ is hydroxyl, $R^4$ is ethyl and $R^5$ is H, 4-desacetyl vincristine is represented; where $R^7$ is CO—$OCH_3$, $R^2$ is methyl, $R^3$ is ethyl, $R^4$ is hydroxyl, and $R^5$ is H, 4-desacetyl leurosidine is represented; where $R^7$ is CO—$OCH_3$, $R^2$ is methyl or formyl, $R^3$ is ethyl and $R^4$ and $R^5$ taken together with the carbons to which they are attached form an alpha-epoxide ring, 4-desacetyl leurosine and 4-desacetyl leuroformine, respectively are represented; where $R^7$ is CO—$OCH_3$, $R^2$ is methyl, $R^3$ is ethyl, $R^4$ and $R^5$ are H, 4desacetyl deoxy VLB "B" or 4-desacetyl-4'-deoxyleurosidine or 4-desacetyl-4'-epideoxy VLB is represented; where $R^7$ is CO—$OCH_3$, $R^2$ is methyl, $R^4$ is ethyl and $R^3$ and $R^5$ are H, 4-desacetyl deoxy VLB "A" or 4-desacetyl-4'-deoxy VLB is represented; where $R^7$ is CO—$OCH_3$, $R^2$ is CHO, $R^3$ is ethyl, $R^4$ and $R^5$ are H, 4-desacetyl-4'-epideoxyvincristine (4-desacetyl-1-formyl-1-desmethyl-4'-deoxyleurosidine) is represented; and where $R^7$ is CO—$NH_2$, $R^2$ is methyl, $R^3$ is OH, $R^4$ is ethyl and $R^5$ is H, vindesine (4-desacetyl-VLB 3-carboxamide) is represented. Other 3-carboxamide derivatives of the 4-desacetyl indole-dihydroindole alkaloids represented by III are named accordingly; i.e., as the 3-(2-methylthio)ethylcarboxamide, as the 3-pyrrolidinyl derivative, as the N-methylcarboxamide derivative, etc. for each of the amide groups comprehended within $R^7$ above. Compounds according to IV in which $R^7$ is a carboxyl group are named as "oic acids"; i.e., 4-desacetyl vinblastinoic acid, 4-desacetyl leurosinoic acid, 4-desacetyl vincristinoic acid, etc.

Literature references to the parent alkaloids of the 4-desacetyl derivatives (III or IV) are as follows: leurosine (U.S. Pat. No. 3,370,057), VLB (U.S. Pat. No. 3,097,137), leurosidine (vinrosidine) and leurocristine (to be referred to hereafter as vincristine) (both U.S. Pat. No. 3,205,220), desmethyl VLB (U.S. Pat. No. 3,354,163), vindesine and other 3-carboxamides (U.S. Pat. No. 4,203,898), vinblastinoic acid, vincristinoic acid, etc. (U.S. Pat. No. 4,012,390), 4'-epivincristine (U.S. Pat. No. 4,143,041) leuroformine, formylleurosine (U.S. Pat. No. 4,279,816), and deoxy VLB "A" and "B" [*Tetrahedron Letters*, 783 (1958)].

The preparation of typical compounds according to formula II is illustrated below. For ease of naming, a compound of the structure R—O—CO—CH$_2$—CH$_2$—COOH, for example, would be designated a VLB 4-hemisuccinate, omitting the 4-desacetyl term as common to all R or R$^{11}$ radicals.

EXAMPLE 1

Preparation of VLB-4-Hemisuccinate

Two g. of 4-desacetyl VLB were dissolved in pyridine to which solution were added 2 g. of succinic anhydride. The reaction mixture was stirred at ambient temperature for 5 hours. (Temperatures in the range 0°–50° C. may be used for this reaction.) The volatile constituents were removed by evaporation in vacuo and the residue taken up in CH$_2$Cl$_2$. The CH$_2$Cl$_2$ layer was washed with 5% aqueous sodium bicarbonate, and then with water. The organic layer was dried and the solvent removed therefrom in vacuo. VLB 4-hemisuccinate thus prepared had the following physical characteristics:

IR: peaks at 1737, 1615, 1460, 1434 cm$^{-1}$.

nmr (CDCl$_3$): 8.05, 7.54, 7.14, 6.58, 6.11, 5.83, 5.46, 5.28, 3.80, 3.78, 3.69, 3.62, 2.71, 0.92, 0.79 ppm.

The sulfate salt was prepared by dissolving VLB hemisuccinate in anhydrous ethanol and 2% ethanolic sulfuric acid added to pH=3.95, and then evaporating the volatile constituents. The sulfate salt had the following physical characteristics:

U.V. (H$_2$O) maximum at 214, 268, 283, 312 nm.

IR (KBr): peaks at 3400 (broad), 1740 cm$^{-1}$.

Titration (66% DMF): pKa=4.80, 6.10, 7.80.

The above procedure was used to prepare the following additional compounds:

Vincristine 4-hemisuccinate from 4-desacetylvincristine; yield=700 mg. (from 1.95 g.). The compound had the following physical characteristics:

IR: peaks at 1740, 1684 cm$^{-1}$.

nmr (CDCl$_3$): 8.77, 8.15, 8.11, 7.72, 7.54, 7.18, 6.90, 6.83, 5.89, 5.39, 5.21, 4.69, 4.51, 3.86, 3.74, 3.67 ppm.

The sulfate salt was prepared by adding 2% ethanolic sulfuric acid to an ethanol solution of the free base (400 mg.); yield=330 mg.; R$_f$(silica gel, methanol)=0.16.

Vindesine 4-hemisuccinate was prepared from 300 mg. of vindesine (4-desacetyl VLB C-3 carboxamide); yield=290 mg. The compound had the following physical characteristics:

IR: peaks at 3450, 1733, 1693 cm$^{-1}$.

nmr (CDCl$_3$): 8.07, 7.52, 7.10, 6.54, 6.08, 5.92, 5.49, 5.27, 3.70, 3.59, 3.46, 2.83, 0.91, 0.78 ppm.

The sulfate salt was prepared as above (200 mg. of free base gave 160 mg. of a white amorphous powder) tlc R$_f$(silica gel, methanol)=0.56.

4'-epideoxy VLB 4-hemisuccinate from 4-desacetyl-4'-epideoxy VLB (1080 mg.); yield=540 mg.; R$_f$(SiO$_2$, 1:1 EtOAc/MeOH)=0.08.

Vinblastinoic acid 4-hemisuccinate from 4-desacetyl vinblastinoic acid. The compound had the following physical characteristics:

R$_f$(SiO$_2$ gel, MeOH)=0.23.

nmr (CDCl$_3$): 8.05, 7.52, 7.11, 6.57, 6.06, 5.71, 5.26, 5.14, 3.75, 3.60, 2.82, 0.90, 0.76 ppm.

Following the above procedure, 4-desacetyl VLB was reacted with maleic anhydride to form VLB 4-hemimaleate. The compound had the following physical characteristics:

IR: peaks at 1730, 1590 cm$^{-1}$.

nmr (CDCl$_3$): 8.61, 8.04, 7.50, 7.12, 6.59, 6.48, 5.78 (J=12 Hz) 6.09, 5.7, 5.51, 5.3, 3.79, 2.70 ppm.

Following the above procedure, VLB 4-hemiglutarate was prepared (700 mg. from 3 g. starting material) with the following physical characteristics:

IR: peaks at 3450, 1736 cm$^{-1}$.

nmr (CDCl$_3$): 8.07, 7.53, 7.13, 6.53, 6.13, 5.83, 5.45, 5.24, 3.80, 3.68, 3.63, 2.69, 0.91, 0.81 ppm.

R$_f$(SiO$_2$, 1:1 EtOAc/MeOH)=0.25 sulfate salt (yield=50%).

R$_f$(SiO$_2$, 1:1 EtOAc/MeOH)=0.08.

In any of the above acylations of a 4-desacetyl indole-dihydroindole vinca dimer, any incidental acylation of the 3-OH can be reversed by treatment with wet silica gel according to the procedure of Hargrove, U.S. Pat. No. 3,392,173. Alternatively, the compounds can be purified from any 3-acyl derivative or other by-products of the reaction by chromatography, conveniently over silica gel using an ethyl acetate/methanol solvent mixture as the eluant.

EXAMPLE 2

Preparation of "Activated" VLB 4-Hemisuccinate

Ninety mg. of VLB 4-hemisuccinate were dissolved in 2 ml. of CH$_2$Cl$_2$. Fifteen λ of N-methyl morpholine were added and the resulting solution cooled to about 0° C. About 20 λ of isobutyl chloroformate were added followed by 20 mg. of N-hydroxysuccinimide. The reaction mixture was heated to reflux for about 15 minutes, and the solvent and other volatile constituents removed by evaporation in vacuo. The gummy residue was used for conjugation with proteins without further purification. The compound had the following structure:

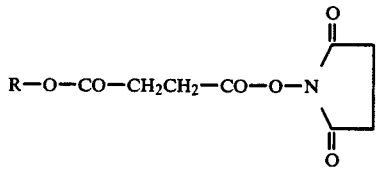

where R is a VLB radical as set forth above. The compound can be named systematically as 4-[3-(1-succinimidooxycarbonyl)]propionyl VLB. It has the following physical characteristics:

IR: (CHCl$_3$) peaks at 1741, 1718 cm$^{-1}$.

In a separate run, the intermediate mixed anhydride of VLB 4-hemisuccinate and isobutylcarbonic acid, having the structure below, was isolated and characterized as follows:

IR: peaks at 3450, 1738, 1820 cm$^{-1}$.

nmr (CDCl$_3$): 8.05, 7.45, 7.15, 6.40, 6.10, 5.88, 5.42, 5.37, 4.00, 3.81, 3.76, 3.65, 2.74, 0.95 ppm.

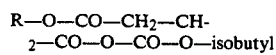

where R is VLB linked to the mixed anhydride function at C-4. An improved method of preparing "activated" VLB 4-hemisuccinate where the activating group is the 1-succinimidoxy group is as follows. One gram of VLB 4-hemisuccinate was mixed with 380 mg. of N-methylmorpholine in 20 ml. of methylenedichloride, and 390 mg. of isobutylchloroformate were added. The reaction mixture was stirred at about 0° C. under a nitrogen atmosphere for about 45 minutes. 795 mg. of N-hydroxysuccinimide were added and the reaction mixture heated at reflux temperature under $N_2$ with stirring for about 45 minutes. The reaction mixture was cooled and the cooled mixture washed with deionized water and then dried immediately with $Na_2SO_4$. The drying agent was separated by filtration and the filtrate evaporated to dryness in vacuo; residue weight=900 mg; tlc indicated 90+% purity.

Following the original procedure, VLB 4-hemiglutarate was treated successively with N-methylmorpholine, isobutylchloroformate and N-hydroxysuccinimide in methylenechloride solution to yield 160 mg. of 4-[4-(1-succinimidoxycarbonyl)]butyryl VLB from 400 mg. of 4-glutaryl VLB.

Following the above procedure, 4'-epideoxy VLB 4-hemisuccinate was converted to 4-[3-(1-succinimidoxycarbonyl)]propionyl VLB. Chromatography over $SiO_2$ gel using 1:1 EtOAc/MeOH; $R_f=0.23$; yield =360 mg. from 540 mg. of starting hemisuccinate.

Following the above procedure, "activated" vindesine 4-hemisuccinate or 4-[3-(1-succinimidoxycarbonyl)]propionyl vindesine was prepared. The compound had the following physical characteristics: IR maxima at 3520, 3470, 3400, 1810, 1791, 1744 with a broad shoulder 1744–1650 $cm^{-1}$.

nmr ($CDCl_3$): 8.08, 7.45, 7.15, 6.44, 6.12, 5.85, 5.48, 5.32, 3.79, 3.64, 3.58, 2.85, 2.84, 0.95, 0.78 ppm.

Also prepared was 4-[3-(1-succinimidoxycarbonyl)]-propionyl vincristine; yield=140 mg. from 256 mg. of starting material. IR peaks at 3460, 1810, 1785, 1744, 1718 and 1683 $cm^{-1}$.

nmr ($CDCl_3$): 8.79, 8.19, 8.14, 7.78, 7.41, 7.18, 6.97, 6.84, 5.92, 5.42, 5.35, 4.72, 4.52, 3.81, 3.78, 3.71, 2.85, 0.83 ppm.

EXAMPLE 3

Preparation of Methyl VLB 4-Hemisuccinate

Two-tenths g. of VLB 4-hemisuccinate were dissolved in 10 ml. of acetic anhydride. Five ml. of glacial acetic acid were added followed by 200 ml. of methanol containing five drops of pyridine. The solution was cooled for one-half hour and then allowed to remain at room temperature for 16 hours. Evaporation of the volatile constituents resulted in an oil. The residue was dissolved in water and the aqueous solution made basic by the addition of 14N aqueous ammonium hydroxide. The basic aqueous layer was extracted with $CH_2Cl_2$. The $CH_2Cl_2$ extract was washed with water and dried. Removal of the solvent left the methyl ester of VLB 4-succinate as a residue (also named as 4-(3-methoxycarbonyl)propionyl VLB.

An improved method of preparing the half methyl ester follows:

1020 mg. of VLB 4-hemisuccinate activated with N-hydroxysuccinimide, as provided by Example 2, were dissolved in 25 ml. of MeOH. The reaction was sealed under $N_2$ and protected from the light. After 18 hours, the volatile constituents were removed in vacuo. The residue was chromatographed on an HPLC silica gel column eluted with a gradient of EtOAc to EtOAc-MeOH (1:1). Fractions containing the desired product, as determined by tlc, were combined. Volatile constituents were removed in vacuo yielding 310 mg. of methyl-4-hemisuccinate VLB as a tan amorphous powder. The sulfate was prepared in the usual manner. (2% $H_2SO_4$ in 2BEtOH).

Other methyl esters prepared by the above procedure include: Methyl vindesine 4-hemisuccinate $R_f(SiO_2$, 1:1 EtOAc/MeOH)=0.5.

IR: peaks at 1735, 1699 $cm^{-1}$.

Mass spectrum: 867 (M+), 836 (M-31), 808 (M-59).

nmr ($CDCl_3$): 9.94, 8.05, 7.52, 7.14, 6.98, 6.58, 6.12, 5.87, 5.53, 5.30, 3.79, 3.69, 3.62, 3.47, 2.74, 0.90, 0.81 ppm.

Sulfate salt: $R_f(SiO_2$, 1:1 EtOAc/MeOH)=0.55 Methyl 4'-epideoxy VLB α-succinate.

Mass spectrum; 866 (M+), 864, 880, 894, 908, 339 (M-vindoline moiety), 139.

IR: peaks at 1743 $cm^{-1}$.

nmr ($CDCl_3$): 8.03, 7.55, 7.16, 6.60, 6.10, 5.89, 5.46, 5.39, 3.82, 3.72, 3.64, 2.76.

EXAMPLE 4

Preparation of 4-Succinoyl VLB Amide

One gram of VLB 4-hemisuccinate was dissolved in about 25 ml. of methylene dichloride. 200 mg. of N-methyl morpholine were added to the solution under a nitrogen atmosphere while the reaction mixture was cooled in an ice bath. 200 mg. of isobutylchloroformate were added and the reaction mixture stirred at room temperature at about 0° C. for 15 minutes. The reaction mixture was then evaporated to dryness to yield a tan gum. The gum was dissolved in methanolic ammonia and kept at ambient temperature under an $N_2$ atmosphere for about 48 hours. Evaporation of the volatile constituents yielded a residue comprising the amide (on the 4-succinate), of VLB 4-hemisuccinate, named as 4-succinoyl VLB amide for convenience. The amide had the following physical characteristics: IR peaks at 1738, 1685 $cm^{-1}$.

Mass Spectrum: 867 (M+), 355, 154.

nmr ($CDCl_3$): 9.86, 8.04, 7.53, 7.12, 6.63, 6.10, 5.85, 5.48, 5.32, 3.81, 3.80, 3.73, 3.62, 2.72, 0.90, 0.82 ppm.

$R_f(SiO_2$, 1:1 EtOAc/MeOH)=0.38.

Sulfate salt: $R_f(SiO_2$, 1:1 EtOAc/MeOH)=0.33.

The corresponding hydrazide, 4-succinoyl VLB hydrazide, was prepared as above by using methanolic hydrazine and a greatly shortened reaction time. The compound had the following physical characteristics:

$R_f(SiO_2$, 1:1 EtOAc/MeOH)=0.23.

IR: peaks at 3400, 3450, 1739, 1680 $cm^{-1}$.

nmr ($CDCl_3$): 9.88, 8.03, 7.53, 7.12, 6.55, 6.10, 5.85, 5.46, 5.27, 3.79, 3.60, 2.30, 0.88, 0.81 ppm.

EXAMPLE 5

Preparation of Methyl VLB 4-Adipoate

One and four-tenths grams of 4-desacetyl VLB were dissolved in 50 ml. of methylene dichloride. Three grams of adipic acid were added followed by 3 g. of dicyclohexylcarbodiimide. The reaction mixture was maintained in a water-free atmosphere at ambient temperature for about 24 hours. The reaction mixture was then filtered and the filter cake washed with methylene dichloride. Evaporation of the methylene dichloride yielded a residue which was purified by chromatography over silica gel using 1:1 ethyl acetate/methanol solvent mixture as the eluant. The major product of the chromatography was methyl VLB 4-adipoate, apparently produced by the presence of unreacted dicyclohexylcarbodiimide and methanol during chromatography; yield=220 mg.; nmr, peak at 3.63 (CH₃O— new methyl ester); mass spectrum; peaks at 910 (M+) 924 (M+14), 879, 852, 355, 154.

The following illustrates the scope of the compounds represented by II above. In naming these compounds, where a group present in the original indole-dihydroindole dimer has been replaced by a new function; i.e., 4-acetoxy replaced by 4-succinoxy or 3-methylcarboxylate by carboxamide, the group removed will be omitted. For example, VLB 4-succinate instead of 4-desacetyl VLB 4-succinate or vindesine 4-succinate for b 4-desacetyl-3-desmethoxycarbonyl VLB 3-carboxamide 4-succinate:

4'-deoxy-4-[3-(1-succinimidoxy)]propionyl VLB
4'-deoxy-4-(3-ethoxycarbonyl)propionyl-1-formyl leurosidine
4'-deoxy-1-formylleurosidine-4-maleate
4'-deoxy-1-formyl-4-(3-azidocarbonyl)propanoyl leurosidine
4-(4-t-butyloxycarbonyl)butynylleurosine
4-[5-(1-phthalimidoxy)]valerylvinblastinoic acid
4-(3-methoxycarbonyl)propiolyl vincristinoic acid
4-[3-(2-benzotriazolyloxy)]propionyl vincristine 3-(2-chloroethyl)carboxamide
4-[(3-trityloxycarbonyl)]propionyl leurosidine 3-(1-pyrrolidyl)carboxamide
4'-deoxy VLB 3-hemiglutarate
leurosine 3-hemiadipate
bis-[4-(4-desacetyl VLB)]succinate
bis-[4-(4-desacetyl VLB 3-carboxamide)]maleate The compounds of this invention in which Z is OR¹, OH, NH₂, NHNH₂, or O—C₁₋₃ alkyl have utility as antitumor compounds active against transplanted tumors in mice. Compounds in which Z is succinimidoxy, phthalimidoxy, Br, Cl, N₃, benzotriazolyloxy, tosyloxy, benzenesulfonyloxy or methanesulfonyloxy are useful in the preparation of antibody conjugates as set forth in the copending application of Cullinan, Rowland and Simmonds Ser. No. 593,443 filed Mar. 26, 1984.

As evidence of the utility of compounds according to I above in which Z is OR¹, OH, NH₂, NHNH₂ or O—C₁₋₃ alkyl as mitotic inhibitors, their ability to cause metaphase arrest was measured by standard procedures. Table I gives the results of this study. In the table, column 1 gives the name of the compound, and column 2 the concentration in the medium of the compound from column 1 in mcg./ml. showing metaphase arrest.

TABLE I

| Name of Compound | Concentration in mcg./ml. Showing Metaphase Arrest |
|---|---|
| 4-Succinoyl VLB amide | 0.2 |
| Methyl VLB 4-hemisuccinate sulfate | 0.02 |
| Methyl vindesine 4-hemisuccinate sulfate | 0.2 |
| VLB 4-hemiglutarate sulfate | 0.2 |
| Vindesine 4-hemisuccinate sulfate | 0.2 |

Certain of the above compounds have also shown activity against transplanted tumors in mice. This information is summarized in Table II in which column 1 gives the name of the compound, column 2 the tumor, column 3 the dose level in mg./kg. and column 4 the percent tumor inhibitor. P1534J is a leukemia and 6C3HED a lymphosarcoma.

TABLE II

| Name Of Compound | Tumor | Dose | Percent Inhibition |
|---|---|---|---|
| Vindesine 4-hemisuccinate | 6C3HED | 12 | 48 |
| | | 25 | 98 |
| | | 50 | 100 |
| VLB 4-hemisuccinate sulfate | P1534J | 18 | 57 |
| | | 36 | Toxic |
| | | 72 | Toxic |
| | 6C3HED | 18 | 100 |
| | | 36 | 100 |
| | | 72 | Toxic |
| Vincristine 4-hemisuccinate sulfate | P1534J | 20 | 63 |
| | | 40 | 83 |
| | | 60 | 94 |
| | | 80 | 96 |
| | 6C3HED | 20 | 100 |
| | | 40 | 100 |
| | | 60 | 100 |
| | | 80 | 100 |

We claim:
1. A compound for the formula:

R—O—CO—X—CO—Z wherein R is a dimeric indole-dihydroindole radical

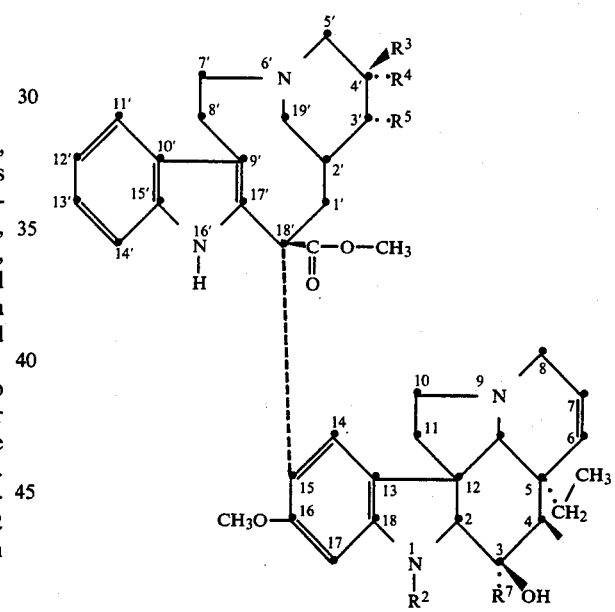

wherein $R^2$ is H, CH₃ or CHO; when $R^4$ and $R^5$ are taken singly, $R^5$ is H, and one of $R^3$ and $R^4$ is ethyl and the other is H or OH; when $R^4$ and $R^5$ are taken together with the carbons to which they are attached, they form an oxirane ring in which $R^3$ is ethyl; and $R^7$ is COOC₁₋₃ alkyl or CO—$R^9$, wherein $R^9$ is NH₂, NH—C₁₋₃ alkyl, NH—CH₂CH₂Cl, 1-pyrrolidyl, 1-piperidinyl, or NH—CH₂CH₂YCH₃ wherein Y is S or O; X is C₁₋₄ straight chain alkylene, C₂₋₈ branched chain alkylene, C₂₋₄ alkenylene, C₃₋₄ alkynylene, C₃₋₆ cycloalkylene, phenylene, hydroxysubstituted C₁₋₄ alkylene or a direct bond, Z is OH, O—C₁₋₃ alkyl, Cl, Br, N₃, NH₂, NH—NH₂, or a carboxy protecting group ($Z^2$), and acid addition salts thereof.

2. A compound according to claim 1 in which Z is OH, NH₂ or OC₁₋₃ alkyl.

3. A compound according to claim 2 in which Z is methoxy.

4. A compound according to claim 2 in which Z is OH.

5. A compound of the formula

R—O—CO—X—CO—Z wherein R is a dimeric indole-dihydroindole radical

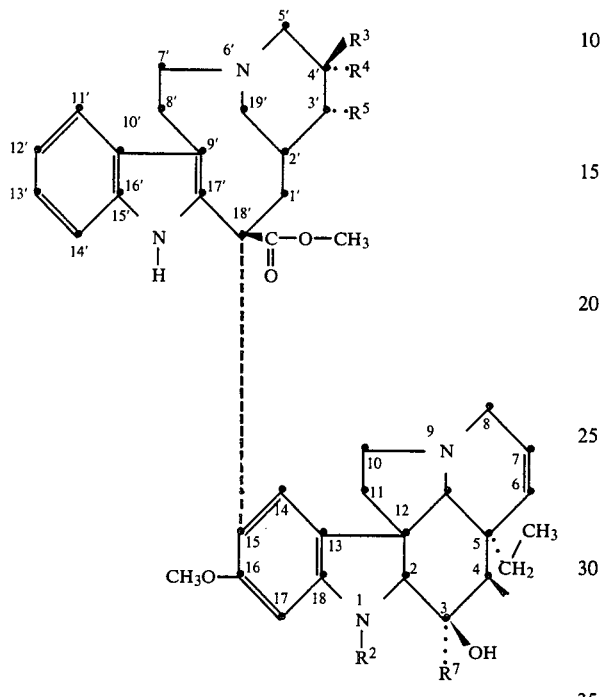

wherein $R^2$ is H, $CH_3$ or CHO; when $R^4$ and $R^5$ are taken singly, $R^5$ is H, and one of $R^3$ and $R^4$ is ethyl and the other is H or OH; when $R^4$ and $R^5$ are taken together with the carbons to which they are attached, they form an oxirane ring in which case $R^3$ is ethyl; and $R^7$ is $COOC_{1-3}$ alkyl or $CO—R^9$, wherein $R^9$ is $NH_2$, $NH—C_{1-3}$ alkyl, $NH—CH_2CH_2Cl$, 1-pyrrolidyl, 1-piperidinyl or $NH—CH_2CH_2YCH_3$ wherein Y is S or O; X is $C_{1-4}$ straight chain alkylene, $C_{2-8}$ branched chain alkylene, hydroxy substituted $C_{1-4}$ alkylene, $C_{2-4}$ alkenylene, $C_{3-4}$ alkynylene, $C_{3-6}$ cycloalkylene, phenylene or a direct bond; Z is OH, $OC_{1-3}$ alkyl, $NH_2$, $NHNH_2$, $Z^1$ or $Z^2$ wherein $Z^1$ is an acylating group and $Z^2$ is a carboxy protecting group.

6. A compound according to claim 5 in which $Z^1$ is Br, Cl, $N_3$, succinimidoxy, phthalimidoxy, benzotriazolyloxy, methanesulfonyloxy, tosyloxy or benzenesulfonyloxy.

7. A compound according to claim 5 in which $Z^2$ is $CCl_3CH_2—O$, $CBr_3CH_2O$, $CH_2ICH_2O$, benzyloxy, methylbenzyloxy, t-butyloxy, allyloxy, methoxybenzloxy, nitrobenzyloxy, phenacyloxy, nitrophenacyloxy, methoxyphenacyloxy, methylphenacyloxy, diphenylmethyloxy, trityloxy, (triphenylmethyloxy), or trimethylsilyloxy.

8. A compound according to claim 5 in which X is $C_{1-4}$ straight chain alkylene.

9. A compound according to claim 5 in which X is $C_{2-4}$ alkenylene.

10. A compound according to claim 8 in which X is $CH_2—CH_2$.

11. A compound according to claim 5, said compound being VLB 4-hemisuccinate.

12. A compound according to claim 5, said compound being VLB 4-hemimaleate.

13. A compound according to claim 5, said compound being vindesine 4-hemisuccinate.

14. A compound according to claim 5, said compound being vincristine 4-hemisuccinate.

15. A compound of the formula $R^{11}$—O—CO—XCO—Z wherein $R^{11}$ is a dimeric indole-dihydroindole radical of the formula

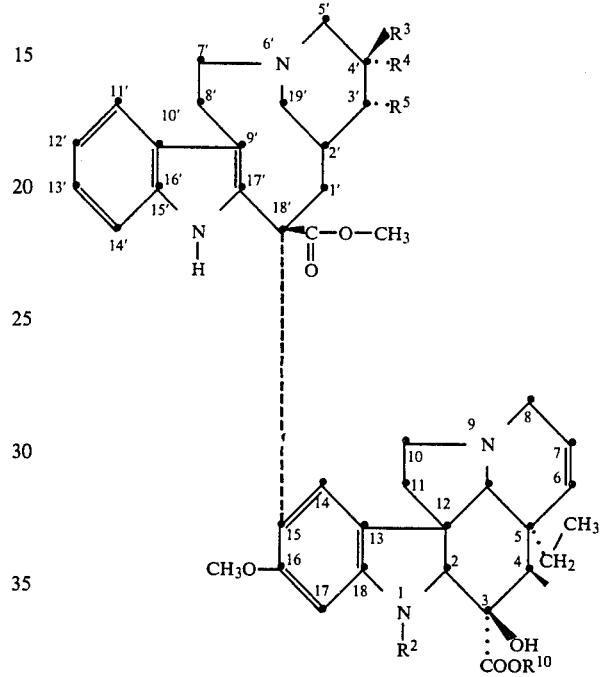

wherein $R^2$ is H, $CH_3$ or CHO; when $R^4$ and $R^5$ are taken singly, $R^5$ is H, and one of $R^3$ and $R^4$ is ethyl and the other is H or OH; when $R^4$ and $R^5$ are taken together with the carbons to which they are attached, they form an oxirane ring in which case $R^3$ is ethyl; and $R^{10}$ is H or $Z^2$; X is $C_{1-4}$ straight chain alkylene, $C_{2-8}$ branched chain alkylene, hydroxy substituted $C_{1-4}$ alkylene, $C_{2-4}$ alkenylene, $C_{3-4}$ alkynylene, $C_{3-6}$ cycloalkylene, phenylene or a direct bond; Z is OH, $OC_{1-3}$ alkyl, $NH_2$, $NHNH_2$, $Z^1$ or $Z^2$ wherein $Z^1$ is an acylating group and $Z^2$ is a carboxy protecting group.

16. A compound according to claim 15 in which Z is Br, Cl, $N_3$, succinimidoxy, phthalimidoxy, benzotriazolyloxy, methanesulfonyloxy, tosyloxy or benzenesulfonyloxy.

17. A compound according to claim 15 in which $Z^2$ is $CCl_3CH_2—O$, $CBr_3CH_2O$, $CH_2ICH_2O$, benzyloxy, methylbenzyloxy, t-butyloxy, allyloxy, methoxybenzloxy, nitrobenzyloxy, phenacyloxy, nitrophenacyloxy, methoxyphenacyloxy, methylphenacyloxy, diphenylmethyloxy, trityloxy, (triphenylmethyloxy), or trimethylsilyloxy.

18. A compound according to claim 15 in which X is $C_{1-4}$ straight chain alkylene.

19. A compound according to claim 15 in which X is $C_{2-4}$ alkenylene.

20. A compound according to claim 18 in which X is $CH_2CH_2$.

21. A compound according to claim 15, said compound being vinblastinoic acid 4-hemisucinate.

* * * * *